US005866602A

United States Patent [19]
Selliah

[11] Patent Number: 5,866,602
[45] Date of Patent: Feb. 2, 1999

[54] KETO-SUBSTITUTED TETRAHYDROFURAN ANALOGS OF PROSTAGLANDINS AS OCULAR HYPOTENSIVES

[75] Inventor: Robert D. Selliah, Fort Worth, Tex.

[73] Assignee: Alcon Laboratories, Inc., Fort Worth, Tex.

[21] Appl. No.: 878,031

[22] Filed: Jun. 18, 1997

Related U.S. Application Data

[60] Provisional application No. 60/009,866 Dec. 22, 1995.
[51] Int. Cl.$^6$ .......................... A61K 31/34; C07D 307/32
[52] U.S. Cl. ............................................. 514/473; 549/475
[58] Field of Search .............................. 514/473; 549/475

[56] References Cited

U.S. PATENT DOCUMENTS

| | | | |
|---|---|---|---|
| 3,883,659 | 5/1975 | Vlattas | 424/285 |
| 4,088,779 | 5/1978 | Vlattas | 424/285 |
| 4,133,817 | 1/1979 | Lourens et al. | 260/340.9 |
| 4,133,948 | 1/1979 | Lourens et al. | 536/1 |
| 4,599,353 | 7/1986 | Bito | 514/530 |
| 5,321,128 | 6/1994 | Stjernschantz et al. | 514/530 |
| 5,574,066 | 11/1996 | Chan et al. | 514/548 |

FOREIGN PATENT DOCUMENTS

| | | |
|---|---|---|
| 0561073 A1 | 9/1993 | European Pat. Off. . |
| 0667160 A2 | 8/1995 | European Pat. Off. . |
| 0686628 A2 | 12/1995 | European Pat. Off. . |
| 2460977 | 1/1976 | Germany . |
| 2601333 A1 | 7/1976 | Germany . |
| 2618861 A1 | 11/1976 | Germany . |
| 2739277 A1 | 3/1978 | Germany . |
| 4229050 A1 | 3/1994 | Germany . |
| 1458164 | 12/1976 | United Kingdom . |
| 1539364 | 1/1979 | United Kingdom . |
| WO 95/26729 | 10/1995 | WIPO . |

OTHER PUBLICATIONS

Alm, "The Potential of Prostaglandin Derivatives in Glaucoma Therapy" *Current Opinion in Ophthalmology* 4(11):44–50 (1993).
Arndt et al., "Stereospecific Synthesis of Modified Prostaglandins Derived from Carbohydrates. Part 1." *S. Afr. J. Chem.* 34(4):121–127 (Jun. 1981).
Flach et al., "Topical Prostaglandin $E_2$ Effects on Normal Human Intraocular Pressure" *Journal of Ocular Pharmacology* 4(1):13–18 (1988).
Giuffre, "The Effects of Prostaglandin $F_{2\alpha}$ the Human Eye" *Graefe's Arch Clin Exp Ophthalmol* 222:139–141 (1985).

Hanessian et al., "Total Synthesis of 11–Oxaprostaglandin $F_{2\alpha}$ and $F_{2\beta}$" *Carbohydrate Research* 141(2):221–238 XP000644751 (1985).
Ichikawa, et al., "Molecular Aspects of the Structures and Functions of the Prostaglandin E Receptors" *J. Lipid Mediators Cell Signaling* 14:83–87 (1996).
Kerstetter et al., "Prostaglandin $F_{2\alpha}$–1–Isopropylester Lowers Intraocular Pressure Without Decreasing Aqueous Humor Flow" *American Journal of Ophthalmology* 105:30–34 (1988).
Lourens et al., "The Novel Stereospecific Synthesis of 11–oxapros–taglandin $F_{2\alpha}$" *Tetrahedron Letters,* No. 43:3719–3722 Pergamon Press (1975).
Nakajima et al., "Effects of Prostaglandin $D_2$ and its Analog, BW245C, on Intraocular Pressure in Humans" *Graefe's Arch Clin Exp Ophthalmol* 229:411–413 (1991).
Theim et al., "Synthese von Qxaprostaglandinen aus 1,4:3, 6–Dianhydro–D–sorbit" *Liebigs Ann. Chem.* 2151:2164 XP0006444761 (1985).
Thierauch et al., "Prostaglandins and Their Receptors: II. Receptor Structure and Signal Transduction" *Journal of Hypertension* 12:1–5 (1994).
Verdoorn et al., "Synthesis of Methyl (5Z,13E(15S)–9α–acetoxy–15–hydroxy–17–(3–trifluoromethylphenyl)–11–oxa–18,19,20–trinorprosta–5,13–dienoate" *S. Afr. Tydskr. Chem.* 40(2):134–138 XP000618452 (1987).
Vlattas et al., "Synthesis of 9–Oxaprostaglandins" *Tetrahedron Letters* No. 51/52:4455–4458, Pergamon Press, 1974.
Vlattas et al., "Synthesis of 11–oxaprostaglandins" *Tetrahedron Letters* No. 51/52:4451–4454, XP000644759, Pergamon Press, 1974.
Waterbury, et al., "$EP_3$, But Not $EP_2$, FP, or TP Prostanoid–Receptor Stimulation May Reduce Intraocular Pressure" *Investigative Ophthalmology and Visual Science* 31(120;2560–2567 (1990).
Woodward, et al, "Intraocular Pressure Effects of Selective Prostanoid Receptor Agonists Involve Different Receptor Subtypes According to Radioligand Binding Studies" *Journal of Lipid Mediators* 6:545–553 c1993).
Woodward et al., "Molecular Characterization and Ocular Hypotensive Properties of the Prostanoid $EP_2$ Receptor" *Journal of Ocular Pharmacology and Therapeutics* 11(3):447–454 (1995).

*Primary Examiner*—Ba K. Trinh
*Attorney, Agent, or Firm*—Barry L. Copeland

[57] ABSTRACT

Keto-substituted tetrahydrofuran analogs of prostaglandins and methods of their use in treating glaucoma and ocular hypertension are disclosed.

10 Claims, No Drawings

KETO-SUBSTITUTED TETRAHYDROFURAN ANALOGS OF PROSTAGLANDINS AS OCULAR HYPOTENSIVES

CROSS-REFERENCE TO RELATED APPLICATIONS

The present application is a continuation-in-part of an earlier filed pending application, International Application Serial No PCT/US96/17900, filed Nov. 12, 1996, which International Application draws priority from U.S. Provisional Application Ser. No. 60/009,866, filed Dec. 22, 1995.

BACKGROUND OF THE INVENTION

The present invention relates to novel compounds and compositions, and methods of their use in the treatment of glaucoma and ocular hypertension. In particular, the present invention relates to the use of certain substituted tetrahydrofuran analogs of E series prostaglandins to treat glaucoma and ocular hypertension.

Glaucoma is a progressive disease which leads to optic nerve damage, and, ultimately, total loss of vision. The causes of this disease have been the subject of extensive studies for many years, but are still not fully understood. The principal symptom of and/or risk factor for the disease is elevated intraocular pressure or ocular hypertension due to excess aqueous humor in the anterior chamber of the eye.

The causes of aqueous humor accumulation in the anterior chamber are not fully understood. It is known that elevated intraocular pressure ("IOP") can be at least partially controlled by administering drugs which reduce either the production of aqueous humor within the eye, such as beta-blockers and carbonic anhydrase inhibitors, or increase the flow of aqueous humor out of the eye, such as miotics and sympathomimetics.

Most types of drugs conventionally used to treat glaucoma have potentially serious side effects. Miotics such as pilocarpine can cause blurring of vision and other visual side effects, which may lead either to decreased patient compliance or to termination of therapy. Systemically administered carbonic anhydrase inhibitors can also cause serious side effects, such as nausea, dyspepsia, fatigue, and metabolic acidosis, which side effects can affect patient compliance and/or necessitate the termination of treatment. Moreover, some beta-blockers have increasingly become associated with serious pulmonary side effects attributable to their effects on beta-2 receptors in pulmonary tissue. Sympathomimetics may cause tachycardia, arrhythmia and hypertension. There is therefore a continuing need for therapies which control the elevated intraocular pressure associated with glaucoma.

Prostaglandins, which are metabolite derivatives of arachidonic acid, have recently been pursued for possible efficacy in lowering IOP. Arachidonic acid in the body is converted to prostaglandin $G_2$, which is subsequently converted to prostaglandin $H_2$. Other naturally occurring prostaglandins are derivatives of prostaglandin $H_2$. A number of different types of prostaglandins have been discovered including A, B, D, E, F, G, I and J-series prostaglandins (EP 0 561 073 A1). Of interest in the present invention are compounds which are believed to exhibit IOP lowering mechanisms similar to those exhibited by $PGE_2$ (formula I):

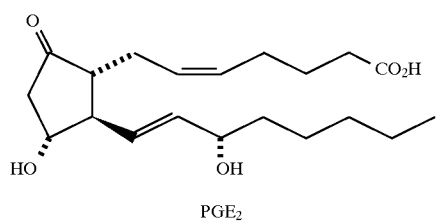

$PGE_2$

The relationship between EP receptor activation and IOP lowering effects is the subject of some debate. There are currently four recognized subtypes of the EP receptor: $EP_1$, $EP_2$, $EP_3$, and $EP_4$ (J. Lipid Mediators Cell Signaling, volume 14, pages 83–87 (1996)). It is known in the art that IOP may be lowered by ligands capable of $EP_2$ receptor activation, such as $PGE_2$ and certain of its synthetic analogs (Journal of Ocular Pharmacology, volume 4, number 1, pages 13–18 (1988); Journal of Ocular Pharmacology and Therapeutics, volume 11, number 3, pages 447–454 (1995)), or $EP_3$ receptor activation (Journal of Lipid Mediators, volume 7, pages 545–553 (1993); Investigative Ophthalmology and Visual Science, volume 31, number 12, pages 2560–2567 (1990)). However, some of these molecules have also been associated with undesirable side effects resulting from topical ophthalmic dosing, including an initial increase in IOP, photophobia, and eye ache (see for example Journal of Ocular Pharmacology, volume 4, number 1, pages 13–18 (1988)).

A number of synthetic prostaglandins have been observed to lower IOP, but such compounds typically produce the aforementioned and other undesirable side effects in varying degrees, which greatly limit their clinical utility. Therefore, a need exists for the development of molecules that may activate the prostaglandin EP receptors, yielding a more efficacious lowering of IOP, while exhibiting fewer or reduced side effects.

An agent which exhibits comparable or improved efficacy, but with reduced side effects when compared to other agents, is said to have an improved therapeutic profile. It is an object of this invention to provide a class of IOP lowering agents with an improved therapeutic profile over endogenous prostaglandins, and methods of their use. Certain 9-keto-11-oxa prostaglandins are disclosed in UK Patent No. 1,539,364. That reference, however, does not disclose the compounds of the present invention, nor does it suggest that such compounds would have an improved therapeutic profile in the treatment of glaucoma and ocular hypertension.

SUMMARY OF THE INVENTION

The present invention is directed to compositions and methods of their use in treating glaucoma and ocular hypertension. In particular, the present invention provides certain classes of keto-substituted tetrahydrofurans which may possess functional EP receptor agonist activity, and methods of their use in treating glaucoma and ocular hypertension.

DETAILED DESCRIPTION OF THE INVENTION

It has unexpectedly been found that the keto-substituted tetrahydrofurans of the present invention exhibit an improved therapeutic profile in the treatment of glaucoma and ocular hypertension when compared to natural prostaglandins and many of their known analogs. The substituted tetrahydrofurans of the present invention are heptanoic acid derivatives having the following formula (II):

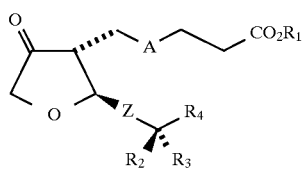

wherein:

$R_1$=H; C1–C5 alkyl or C3–C6 cycloalkyl; a cationic salt moiety;

A=$CH_2CH$=CH (cis olefin), CH=$CHCH_2$ (cis olefin), or $CH_2CH_2CH_2$;

Z=C≡C, trans CH=CH, or $CH_2CH_2$;

one of $R_2$ and $R_3$=H, and the other=F or OH, where the OH may be free or functionally modified; or $R_2$ and $R_3$ taken together=$OCH_2CH_2O$ or double bonded O (carbonyl); and $R_4$=$(CH_2)_m$Xphenyl or $(CH_2)_p Z^2$, where X=O or $CH_2$; m=1–6; the phenyl is either unsubstituted or substituted with $R_5$, where $R_5$=halogen, $CH_3$, $CF_3$, CN, $OCH_3$ or acetyl; p=0–6; and $Z^2$

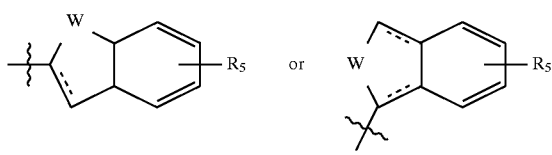

wherein:

W=O, $CH_2$, $CH_2CH_2$, or CH=CH; and $R_5$ is as defined above.

For purposes of the foregoing and following definitions, the term "pharmaceutically acceptable ester moiety" means any ester moiety that would be suitable for therapeutic administration to a patient by any conventional means without significant deleterious health consequences. Similarly, the term "ophthalmically acceptable ester moiety" means any pharmaceutically acceptable ester moiety that would be suitable for ophthalmic application, i.e. non-toxic and non-irritating. Preferred are ophthalmically acceptable esters such as alkyl and alkylcycloalkyl esters of carboxylic acids. Most preferred are $C_2$–$C_5$ alkyl esters of carboxylic acids, and especially isopropyl esters.

Especially preferred compounds of this invention are:

In the foregoing illustrations, as well as those provided hereinafter, wavy line attachments indicate that the configuration may be either alpha (α) or beta (β). The dashed lines on bonds between carbons, e.g. in the bicyclic structural formula for $Z^2$, indicate a single or double bond. Two solid lines present between carbons specify the configuration of the relevant double bond. Hatched lines indicate the α configuration, and a solid triangular line indicates the β configuration.

In the following Example 1, the following standard abbreviations are used: g=grams (mg=milligrams); mol=moles (mmol=millimoles); mL=milliliters; mm Hg=millimeters of mercury; mp=melting point; bp=boiling point; h=hours; and min=minutes. In addition, "NMR" refers to nuclear magnetic resonance spectroscopy and "MS" refers to mass spectrometry.

EXAMPLE 1

Syntheses of Isopropyl [2R(1E, 3R), 3R]-7-[Tetrahydro-2-(4-phenoxy-3-hydroxy-1-butenyl)-4-oxo-3-furanyl]heptanoate (III) and [2R(1E, 3R), 3R]-7-[Tetrahydro-2-(4-phenoxy-3-hydroxy-1-butenyl)-4-oxo-3-furanyl]heptanoic Acid (IV).

Compounds III and IV contained in this invention may be prepared according to the scheme outlined below. The starting material 1 used in this synthesis can be prepared according to published methods (Arndt, et al. *S. Afr. J. Chem.*, 34: 121–127 (1981); U.S. Pat. No. 4,133,948).

Scheme 1: Syntheses of compounds III and IV

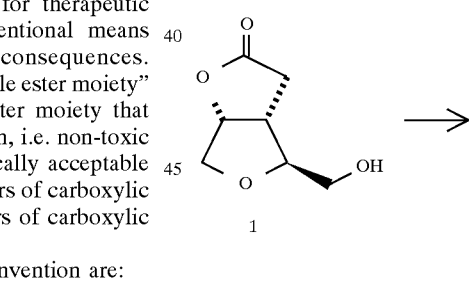

| Compound Number | Compound Name | Compound Structure |
|---|---|---|
| III | Isopropyl [2R(1E, 3R), 3R]-7-[Tetrahydro-2-(4-phenoxy-3-hydroxy-1-butenyl)-4-oxo-3-furanyl]heptanoate | 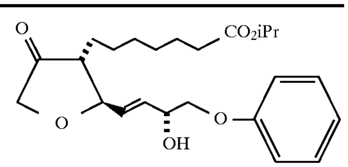 |
| IV | [2R(1E, 3R), 3R]-7-[Tetrahydro-2-(4-phenoxy-3-hydroxy-1-butenyl)-4-oxo-3-furanyl]heptanoic acid | 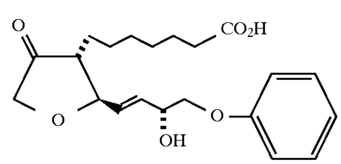 |

Scheme 1: Syntheses of compounds III and IV

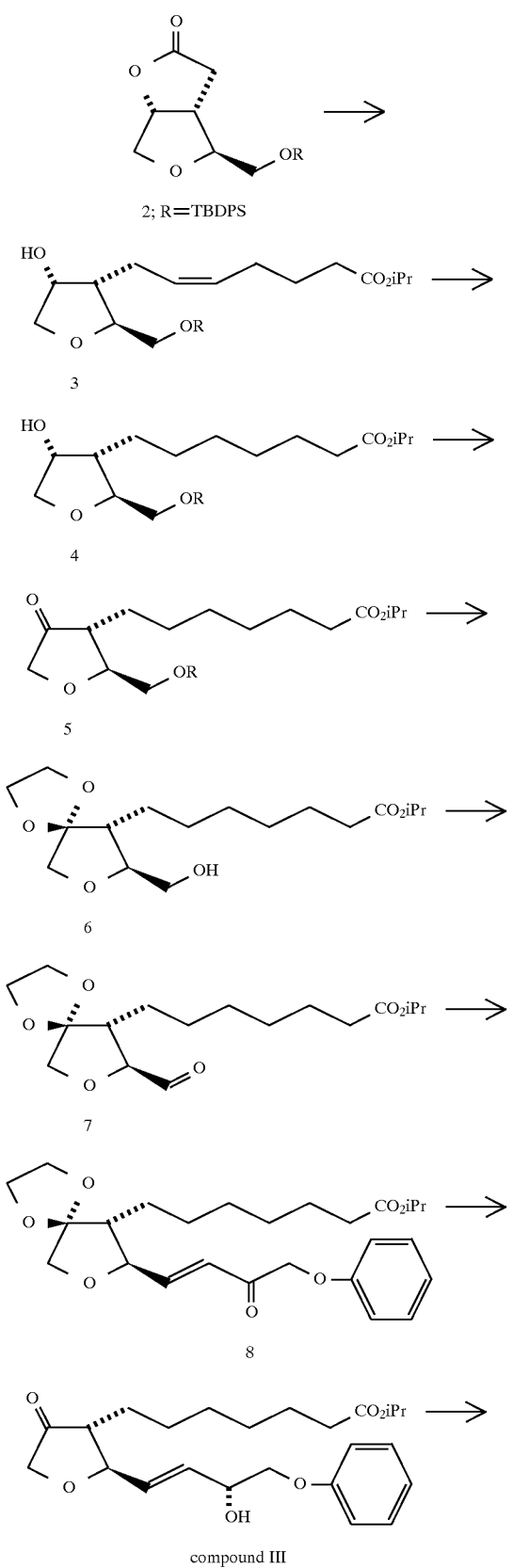

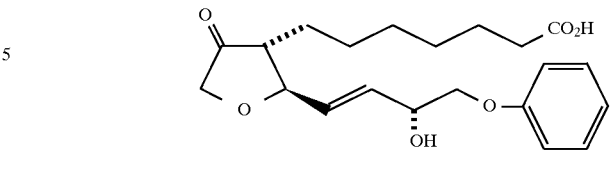

compound IV

A: (3aR,4S,6aR)-4-(tert-Butyldiphenylsilyloxy)methylhexahydrofuro [3,4-b]furan-2-one (2)

A mixture of alcohol 1 (5.0 g, 31.6 mmol) and imidazole (4.3 g, 63.2 mmol) was dissolved in 100 mL of anhydrous DMF. To this solution tert-butyldiphenylsilyl chloride (10.4 g, 38.0 mmol) was added and the resulting mixture was stirred at room temperature for 14 h. The solvent was evaporated and the residue was taken up in 100 mL of EtOAc, washed with water (2×50 mL), dilute aqueous solution of HCl (2×50 mL) and brine and dried (MgSO4). The solvent was evaporated and the crude was purified by chromatography on silica gel to afford 2 (12.4 g, quantitative yield) as a white solid: $R_f$ 0.6 (60% EtOAc/hexanes); $^1$H-NMR (CDCl$_3$) δ7.65 (m, 4H), 7.42 (m, 6H), 5.10 (m, 1H), 4.25 (dd, J=12, 4 Hz, 1H), 4.05 (dd, J=12, 2 Hz, 1H), 3.85 (m, 1H), 3.75 (m, 2H), 3.00 (m, 1H), 2.82 (dd, J=16, 7 Hz, 1H), 2.45 (dd, J=16, 2 Hz, 1H), 1.05 (s, 9H).

B: Isopropyl [2S,3S(5Z),4R]-7-[Tetrahydro-2-(tert-butyldiphenylsilyloxy)methyl-4-hydroxy-3-furanyl]-5-heptenoate (3)

A solution of the lactone 2 (5.7 g, 14.5 mmol) in 150 mL of anhydrous THF was cooled to −78° C. under an inert atmosphere, and to it DIBAL-H (14.5 mL, 1.5M in toluene, 21.7 mmol) was added dropwise. The resulting mixture was stirred at −78° C. for 1.5 h and was then quenched at the same temperature by the addition of 5 mL of methanol. The reaction was warmed to room temperature, an equal volume of a saturated aqueous solution of potassium sodium tartrate was added to it and the resulting slurry was stirred at room temperature for 1 h. The layers were separated, and the aqueous layer was extracted with 3×25 mL of EtOAc. The organic layers were combined and washed with brine and dried (MgSO$_4$). The solution was filtered and concentrated and the crude was purified by passage through a short column of silica gel to afford the intermediate lactol (5.6 g, quantitative yield) as a colorless oil, which was used in the next step: $R_f$ 0.5 (60% EtOAc/hexanes).

To a suspension of (4-carboxybutyl)triphenylphosphonium bromide (12.2 g, 27.6 mmol) in 200 mL anhydrous THF at 0° C., potassium tert-butoxide (t-BuOK, 55.2 mL, 1.0M THF, 55.2 mmol) was added dropwise and the mixture was stirred at 0° C. for 30 min. A solution of the lactol obtained above (5.5 g, 13.8 mmol) in 300 mL of THF was then added to it dropwise. The resulting mixture was allowed to warm to room temperature and was stirred at that temperature for 16 h. The reaction was quenched by pouring it into 250 mL of a 0.5N aqueous HCl solution and the mixture was extracted with EtOAc (5×50 mL). The combined organic extracts were washed with water (1×25 mL) and brine (1×25 mL) and dried over anhydrous Na$_2$SO$_4$. The solution was filtered, concentrated and the crude residue thus obtained was taken up in 100 mL of acetone and cooled to 0° C. To this, 1,8-diazabicyclo

[5.4.0]undec-7-ene (12.5 mL, 83 mmol) was added and the mixture was stirred at 0° C. for 30 min. At this time, 2-iodopropane (6.8 mL, 69 mmol) was added, the cold temperature bath was romoved and the reaction was stirred at room temperature for 16 h. Solvent was then evaporated and the residue was taken up in 50 mL of 0.5N aqueous HCl and this solution was extracted with 5×50 mL of ether. Combined organic extracts were washed with water and brine and dried over $MgSO_4$. Solvent removal and chromatography of the crude on silica afforded the desired isopropyl ester 3 (6.2 g, 87% yield) as a colorless oil: $R_f$0.46 (60% EtOAc/hexane); $^1$H-NMR (CDCl$_3$) δ7.69 (m, 4H), 7.40 (m, 6H), 5.40 (m, 2H), 5.00 (septet, J=6.4 Hz, 1H), 4.22 (m, 1H), 4.00–3.62 (broad m, 5H), 2.40–1.50 (broad m, 12H), 1.23 (d, J=7.2 Hz, 6H), 1.05 (s, 9H).

C: Isopropyl [2S,3S,4R]-7-[Tetrahydro-2-(tert-butyldiphenylsilyloxy)methyl-4-hydroxy-3-furanyl] heptanoate (4)

A solution of the ester 3 (2.0 g, 3.8 mmol) in 50 mL of EtOAc was subjected to hydrogenation at atmospheric pressure in the presence of Pd on carbon as the catalyst (10% Pd content, 100 mg) for 16 h. Filtration, solvent removal and purification of the crude by passage through a short plug of silica gel afforded the reduction product 4 (1.92 g, 96% yield) as a colorless liquid: $R_f$0.46 (60% EtOAc/hexane); $^1$H-NMR (CDCl$_3$) δ7.69 (m, 4H), 7.40 (m, 6H), 5.00 (septet, J=6.4 Hz, 1H), 4.30 (m, 1H), 4.00–3.60 (broad m, 5H), 2.25 (t, J=6.8 Hz, 2H), 2.10 (m, 1H), 1.59 (broad m, 4H), 1.29 (broad m, 4H), 1.24 (d, J=7.2 Hz, 6H), 1.05 (s, 9H).

D: Isopropyl [2S,3R]-7-[Tetrahydro-2-(tert-butyldiphenylsilyloxy)methyl-4-oxo-3-furanyl] heptanoate (5)

A dry 100 mL round-bottom flask was charged with 15 mL of anhydrous CH$_2$Cl$_2$ and oxalyl chloride (2.8 mL, 2.0M in CH$_2$Cl$_2$, 5.6 mmol) and this solution was cooled to −78° C. A solution of DMSO (0.78 mL, 11.0 mmol) in 5 mL of CH$_2$Cl$_2$ was added dropwise and the resulting solution was stirred for 3 min. To this mixture, a solution of the alcohol 4 (1.92 g, 3.65 mmol) in 30 mL of CH$_2$Cl$_2$ was added dropwise and stirring was continued for 15 min. Triethylamine (1.5 mL, 11.0 mmol) was then introduced dropwise and the mixture was allowed to warm to room temperature over 15 min. The reaction mixture was poured into 50 mL of water, the layers were separated and the aqueous layer was extracted with 50 mL of CH$_2$Cl$_2$. The combined organic extracts were washed with water and brine, and dried over anhydrous MgSO$_4$. Filtration, solvent removal and chromatography of the crude on silica gel afforded the ketone 5 (1.9 g, 99% yield) as pale yellow oil: $R_f$0.7 (60% EtOAc/hexane); $^{13}$C-NMR (CDCl$_3$) δ217.04, 173.21, 135.59, 132.99, 129.83, 129.77, 127.75, 127.72, 83.48, 71.34, 67.34, 65.79, 47.87, 34.61, 29.23, 28.83, 28.29, 26.89, 26.75, 24.90, 21.84, 19.19.

E: Isopropyl [2S,3R]-7-[Tetrahydro-2-hydroxymethyl-4.4-ethylenedioxy-3-furanyl] heptanoate (6)

A solution of TMSOTf (6 μL, 0.03 mmol) in 3.0 mL of anhydrous CH$_2$Cl$_2$ was cooled to −78° C. and to it 1,2-bis (trimethylsilyloxy)ethane (1.0 mL, 4.4 mmol) was introduced dropwise. This was immediately followed by the addition of the ketone 5 (1.54 g, 2.94 mmol) as a solution in 5.0 mL of CH$_2$Cl$_2$. The resulting mixture was stirred at −78° C. for 3 h and was then placed in a freezer at −20° C. (without stirring) for 16 h. The mixture was removed from the freezer, cooled to −78° C., and treated with 3.0 mL of anhydrous pyridine. After warming to room temperature, the mixture was partitioned between EtOAc and saturated aqueous NaHCO$_3$. The organic layer was dried over anhydrous K$_2$CO$_3$ and processed normally and the crude material obtained was used in the subsequent step.

The crude silyl ether thus obtained was taken up in 30 mL of THF and the solution was treated with tetra-n-butylammonium fluoride (30 mL, 1.0M in THF, 30 mmol) at room temperature for 30 min. The mixture was then poured into 50 mL of water and extracted with 4×25 mL of EtOAc. Combined organic extracts were washed with water, dilute aqueous solution of CuSO$_4$ and brine and dried over MgSO$_4$. Filtration, solvent removal and chromatography of the crude on silica gel afforded the desired compound 6 (0.88 g, 90% yield for two steps) as a pale yellow liquid: $R_f$0.2 (60% EtOAc/hexane); $^1$H-NMR (d$_6$-DMSO) δ4.85 (septet, J=6.4 Hz, 1H), 4.66 (t, J=5.3 Hz, 1H, OH), 3.83 (broad m, 4H), 3.58–3.25 (broad m, 6H), 2.05 (t, J=7.2 Hz, 2H), 1.95 (m, 1H), 1.45 (broad m, 3H), 1.22 (broad m, 7H), 1.13 (d, J=7.3 Hz, 6H).

F: Isopropyl [2S,3R]-7-[Tetrahydro-2-formyl-4,4-ethylenedioxy-3-furanyl]heptanoate (7)

A solution of oxalyl chloride (2.0 mL, 2.0M in CH$_2$Cl$_2$, 4.0 mmol) in 15 mL of CH$_2$Cl$_2$ was cooled to −78° C., and to it a solution of DMSO (0.5 mL, 7.8 mmol) in 1.0 mL of CH$_2$Cl$_2$ was added dropwise. The resulting solution was stirred for 3 min, at which time a solution of the alcohol 6 (0.88 g, 2.6 mmol) in 15 mL of CH$_2$Cl$_2$ was introduced via cannula. Stirring was continued at −78° C. for 15 min and then triethyl amine (1.8 mL, 13 mmol) was added. The mixture was allowed to warm to room temperature over a period of 10 min and was then poured into 50 mL of water. The layers were separated and the aqueous layer was extracted with 25 mL of CH$_2$Cl$_2$. Combined organic extracts were washed with water, brine and dried (MgSO$_4$) and processed in the normal manner. The crude material was subjected to chromatography on silica gel to yield the aldehyde 7 (0.75 g, 88% yield) as a pale yellow liquid: $R_f$0.4 (60% EtOAc/hexane); $^1$H-NMR (d$_6$-DMSO) δ9.58 (d, J=1.3 Hz, 1H), 4.85 (septet, J=6.2 Hz, 1H), 4.05 (m, 1H), 3.84 (broad m, 4H), 3.66 (s, 2H), 3.50 (m, 1H), 2.20 (m, 4H), 1.47 (m, 4H), 1.22 (broad m, 6H), 1.16 (d, J=7.2 Hz, 6H).

G: Isopropyl [2R(1E), 3R]-7-[Tetrahydro-2-(4-phenoxy-3-oxo-1-butenyl)-4,4-ethylenedioxy-3-furanyl]heptanoate (8)

A solution containing dimethyl-3-phenoxy-2-oxopropylphosphonate (1.47 g, 5.7 mmol) and LiCl (0.24 g, 5.7 mmol) in 10 mL of anhydrous THF was cooled to 0° C. under an inert atmosphere and to it triethylamine (0.8 mL, 5.7 mmol) was added dropwise. The resulting white slurry was stirred for 10 min at 0° C., and then a solution of the aldehyde 7 (0.75 g, 2.28 mmol) in 10 mL of THF was introduced via cannula. The reaction was allowed to warm to room temperature gradually and stirred at that temperature for 18 h. The mixture was then poured into 50 mL of water and extracted with 4×25 mL of EtOAc. Combined organic extracts were washed with brine and dried (MgSO$_4$) and processed in the normal way, and the crude material was subjected to chromatography on silica gel to afford the enone 8 (0.38 g, 28% yield) as a colorless liquid: $R_f$0.3 (30% EtOAc/hexane); $^1$H-NMR (d$_6$-DMSO) δ7.28 (m, 2H), 7.05–6.87 (broad m, 4H), 6.55 (d, J=16 Hz, 1H), 5.02 (s, 2H), 4.85

(septet, J=6.4 Hz, 1H), 4.28 (m, 1H), 3.80–3.50 (broad m, 6H), 2.21 (t, J=6.2 Hz, 2H), 2.00 (m, 1H), 1.50 (m, 4H), 1.23 (broad m, 6H), 1.17 (d, J=7.0 Hz, 6H).

H: Isopropyl [2R(1E, 3R), 3R]-7-[Tetrahydro-2-(4-phenoxy-3-hydroxy-1-butenyl)-4-oxo-3-furanyl] heptanoate (III)

A solution containing the enone 7 (0.23 g, 0.5 mmol) and $CeCl_3 \cdot 7H_2O$ (0.37 g, 1.0 mmol) in 30 mL of methanol was cooled to 0° C. $NaBH_4$ (37 mg, 1.0 mmol) was added to this solution in small portions over a period of 3 min. After the addition was complete, the reaction mixture was stirred for 5 min at 0° C. and then quenched by treating with 5 mL of a 1N HCl solution. The slurry thus formed was poured into saturated aqueous $NaHCO_3$ (50 mL) and extracted with EtOAc (4×10 mL). The combined organic extracts were washed with water and brine and dried ($MgSO_4$). Filtration and solvent removal gave 0.24 g of the crude intermediate which was used in the next step without further purification.

The crude material obtained above (0.24 g) and a catalytic amount of p-TsOH (50 mg) were dissolved in a mixture of 20 mL of acetone and 0.2 mL of water. The solution was heated at reflux for 18 h and then cooled to room temperature. Solvent was evaporated and the residue was partitioned between 50 mL of EtOAc and saturated aqueous $NaHCO_3$. The organic layer was washed with water and brine and dried ($MgSO_4$). Filtration, solvent removal and chromatography of the crude on normal phase HPLC afforded compound III (64 mg, 30% yield, for two steps) as a colorless liquid: : $R_f 0.4$ (60% EtOAc/hexane); $^1$H-NMR ($CDCl_3$) δ7.29 (m, 2H), 6.93 (m, 3H), 6.01 (m, 2H), 5.00 (septet, J=6.4 Hz, 1H), 4.62 (m, 1H), 4.35 (m, 1H), 4.25–3.80 (broad m, 4H), 2.60 (m, 1H), 2.23 (m, 3H), 1.63–1.30 (broad m, 10H), 1.23 (d, J=7.2 Hz, 6H); $^{13}$C-NMR ($CDCl_3$) δ215.97, 173.30, 158.33, 132.06, 130.81, 129.54, 121.34, 114.58, 83.19, 71.47, 71.00, 70.00, 67.41, 52.47, 34.55, 29.19, 28.72, 26.62, 24.82, 21.83 ; HRMS (FAB) calcd. for $C_{24}H_{34}O_6Na$ (M+Na), 441.223470, found 441.22348; $[\alpha]_{405} -101°$ (c=0.07).

I: [2R(1E, 3R), 3R]-7-[Tetrahydro-2-(4-phenoxy-3-hydroxy-1-butenyl)-4-oxo-3-furanyl]heptanoic Acid (IV)

A solution containing compound III (34 mg, 0.08 mmol), $LiOH \cdot H_2O$ (34 mg, 0.80 mmol), $CH_3OH$ (3.0 mL) and water (1.0 mL) was stirred at room temperature for 2 h and then poured into 50 mL each of 1N aqueous HCl solution and $CHCl_3$. The layers were separated, and the aqueous layer was extracted with 3×20 mL of $CHCl_3$. Combined organic extracts were washed with water (2×25 mL) and brine and dried ($Na_2SO_4$). Filtration and concentration afforded a residue which was taken up in 3.0 mL of $CH_3CN$ and the solution was filtered through a 0.45 micron nylon membrane filter. The filtrate was concentrated to afford compound IV (32 mg, quantitative yield) as a colorless liquid: $^{13}$C-NMR ($CDCl_3$) δ216.03, 178.28, 158.39, 131.99, 130.92, 129.63, 121.46, 114.69, 83.27, 71.52, 71.10, 70.12, 52.39, 33.71, 28.96, 28.56, 26.56, 26.51, 24.53 ; HRMS (FAB) calcd. for $C_{21}H_{28}O_6Na$ (M+Na) 399.177448, found 399.17746.

The substituted tetrahydrofurans of the present invention may be formulated in various pharmaceutical compositions for administering to humans and other mammals as a treatment of glaucoma or ocular hypertension. As used herein, the term "pharmaceutically effective amount" refers to that amount of a compound of the present invention which lowers IOP when administered to a patient, especially a mammal. The preferred route of administration is topical. The compounds of the present invention can be administered as solutions, suspensions, or emulsions (dispersions) in an ophthalmically acceptable vehicle. As used herein, the term "ophthalmically acceptable vehicle" refers to any substance or combination of substances which are non-reactive with the compounds and suitable for administration to a patient. Solubilizers and stabilizers are deemed to be non-reactive. Preferred are aqueous vehicles suitable for topical application to the patient's eyes.

In forming compositions for topical administration, the compounds of the present invention are generally formulated as between about 0.00003 to about 0.5 percent by weight (wt %) solutions in water at a pH between about 4.5 to about 8.0, preferably between about 5.0 and about 7.5. The compounds are preferably formulated as between about 0.0005 to about 0.03 wt % and, most preferably, between about 0.001 and about 0.01 wt %. While the precise regimen is left to the discretion of the clinician, it is recommended that the resulting solution be topically applied by placing one drop in each eye one or two times a day.

Other ingredients which may be desirable to use in the ophthalmic preparations of the present invention include preservatives, co-solvents, and viscosity building agents.

Antimicrobial Preservatives

Ophthalmic products are typically packaged in multidose form. Preservatives are thus required to prevent microbial contamination during use. Suitable preservatives include: benzalkonium chloride, thimerosal, chlorobutanol, methyl paraben, propyl paraben, phenylethyl alcohol, edetate disodium, sorbic acid, Onamer M, or other agents known to those skilled in the art. Such preservatives are typically employed at a level between about 0.001% and about 1.0% by weight.

Co-Solvents

Prostaglandins, and particularly ester derivatives, typically have limited solubility in water and therefore may require a surfactant or other appropriate co-solvent in the composition. Such co-solvents include: Polysorbate 20, 60 and 80; Pluronic F-68, F-84 and P-103; CREMOPHORE® EL (polyoxyl 35 castor oil); cyclodextrin; or other agents known to those skilled in the art. Such co-solvents are typically employed at a level between about 0.01% and about 2% by weight.

Viscosity Agents

Viscosity greater than that of simple aqueous solutions may be desirable to increase ocular absorption of the active compound, to decrease variability in dispensing the formulations, to decrease physical separation of components of a suspension or emulsion of formulation and/or otherwise to improve the ophthalmic formulation. Such viscosity building agents include, for example, polyvinyl alcohol, polyvinyl pyrrolidone, methyl cellulose, hydroxy propyl methylcellulose, hydroxyethyl cellulose, carboxymethyl cellulose, hydroxy propyl cellulose, chondroitin sulfate and salts thereof, hyaluronic acid and salts thereof, and other agents known to those skilled in the art. Such agents are typically employed at a level between about 0.01% and about 2% by weight.

Preferred formulations of substituted tetrahydrofurans of the present invention include the following Examples 2–4:

EXAMPLE 2

| Ingredient | Amount (wt %) |
| --- | --- |
| Compound III | 0.01 |
| Monobasic sodium phosphate | 0.05 |
| Dibasic sodium phosphate (anhydrous) | 0.15 |
| Sodium chloride | 0.75 |
| Disodium EDTA (Edetate disodium) | 0.05 |
| Cremophor ® EL | 0.1 |
| Benzalkonium chloride | 0.01 |
| HCl and/or NaOH | q.s. pH 7.3–7.4 |
| Purified water | q.s. 100% |

EXAMPLE 3

| Ingredient | Amount (wt %) |
| --- | --- |
| Compound III | 0.003 |
| Sodium acetate (trihydrate) | 0.07 |
| Mannitol | 4.3 |
| Disodium EDTA (Edetate disodium) | 0.1 |
| Cremophor ® EL | 0.5 |
| Benzalkonium chloride | 0.01 |
| HCl and/or NaOH | q.s. pH 5.0 |
| Purified water | q.s. 100% |

EXAMPLE 4

| Ingredient | Amount (wt %) |
| --- | --- |
| Compound III | 0.05 |
| Phosphate Buffered Saline | 1.0 |
| Hydroxypropyl-β-cyclodextrin | 4.0 |
| Purified water | q.s. 100% |

The invention has been described by reference to certain preferred embodiments; however, it should be understood that it may be embodied in other specific forms or variations thereof without departing from its spirit or essential characteristics. The embodiments described above are therefore considered to be illustrative in all respects and not restrictive, the scope of the invention being indicated by the appended claims rather than by the foregoing description.

What is claimed is:

1. A method of treating glaucoma or ocular hypertension in a patient, which comprises administering to the patient a pharmaceutically effective amount of a compound of formula (II):

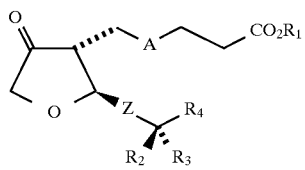

wherein:

$R_1$=H; C1–C5 alkyl or C3–C6 cycloalkyl; a cationic salt moiety;

A=$CH_2CH=CH$ (cis olefin), $CH=CHCH_2$ (cis olefin), or $CH_2CH_2CH_2$;

Z=C≡C, trans CH=CH, or $CH_2CH_2$;

one of $R_2$ and $R_3$=H, and the other=F or OH, where the OH may be free or functionally modified; or $R_2$ and $R_3$ taken together=$OCH_2CH_2O$ or double bonded O (carbonyl); and $R_4$=$(CH_2)_m$Xphenyl or $(CH_2)_p$ $Z^2$, where X=O or $CH_2$; m=1–6; the phenyl is either unsubstituted or substituted with $R_5$, where $R_5$=halogen, $CH_3$, $CF_3$, CN, $OCH_3$ or acetyl; p=0–6; and $Z^2$=

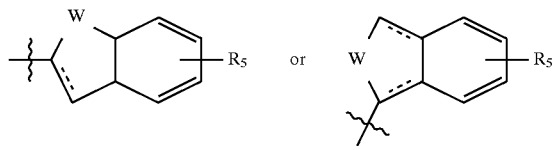

wherein:

W=O, $CH_2$, $CH_2CH_2$, or CH=CH; and $R_5$ is as defined above.

2. The method of claim 1, where the compound is administered topically.

3. The method of claim 2, wherein the compound is administered as a solution, suspension, or emulsion.

4. The method of claim 3, wherein $R_1$ is selected from the group consisting of: isopropyl and neopentyl esters of carboxylic acids.

5. The method of claim 4, wherein the concentration of the compound is between about 0.00003 to about 0.5 weight percent.

6. The method of claim 5, wherein the concentration of the compound is between about 0.0005 to about 0.03 weight percent.

7. The method of claim 6, wherein the concentration of the compound is between about 0.001 and about 0.01 weight percent.

8. A compound of formula (II):

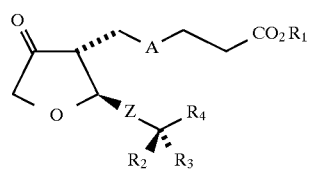

wherein:

$R_1$=H; C1–C5 alkyl or C3–C6 cycloalkyl; a cationic salt moiety;

A=$CH_2CH=CH$ (cis olefin), $CH=CHCH_2$ (cis olefin), or $CH_2CH_2CH_2$;

Z=C≡C, trans CH=CH, or $CH_2CH_2$;

one of $R_2$ and $R_3$=H, and the other=F or OH, where the OH may be free or functionally modified; or $R_2$ and $R_3$ taken together=$OCH_2CH_2O$ or double bonded O (carbonyl); and $R_4$=$(CH_2)_m$Xphenyl or $(CH_2)_p$ $Z^2$, where X=O or $CH_2$; m=1–6; the phenyl is either unsubstituted or substituted with $R_5$, where $R_5$=halogen, $CH_3$, $CF_3$, CN, $OCH_3$ or acetyl; p=0–6; and $Z^2$=

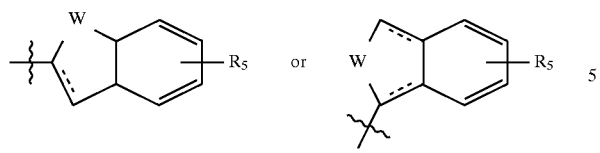

wherein:
W=O, $CH_2$, $CH_2CH_2$, or CH=CH; and $R_5$ is as defined above;

with the proviso that the following compounds of formula (II) be excluded; those wherein:
$R_1$=H, alkyl, cycloalkyl or aryl;
A=CH=CHCH$_2$ (cis olefin) or $CH_2CH_2CH_2$;
Z=trans CH=CH or $CH_2CH_2$;
one of $R_2$ and $R_3$=H, and the other=OH; and
$R_4$=CH$_2$Xphenyl, where X=O or $CH_2$; and the phenyl is either unsubstituted or substituted with $R_5$, where $R_5$=F, Cl, $CH_3$, or $OCH_3$.

9. An ophthalmic composition for the topical treatment of glaucoma and ocular hypertension, comprising a compound of formula (II):

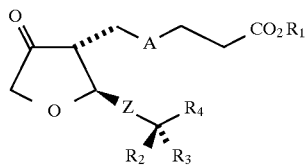

wherein:
$R_1$=H, C1–C5 alkyl, C3–C6 cycloalkyl, or a cationic salt moiety;
A=$CH_2$CH=CH (cis olefin), CH=CHCH$_2$ (cis olefin), or $CH_2CH_2CH_2$;
Z=C≡C, trans CH=CH, or $CH_2CH_2$;
one of $R_2$ and $R_3$=H, and the other=F or OH, where the OH may be free or functionally modified; or $R_2$ and $R_3$ taken together=OCH$_2$CH$_2$O or double bonded O (carbonyl); and
$R_4$=(CH$_2$)$_m$Xphenyl or (CH$_2$)$_p$ $Z^2$, where X=O or $CH_2$; m=1–6; the phenyl is either unsubstituted or substituted with $R_5$, where $R_5$=halogen, $CH_3$, $CF_3$, CN, $OCH_3$ or acetyl; p=0–6; and $Z^2$=

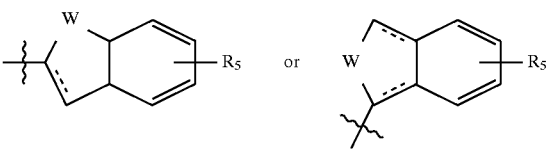

wherein:
W=O, $CH_2$, $CH_2CH_2$, or CH=CH; and $R_5$ is as defined above;

and an ophthalmically acceptable vehicle therefor; wherein said composition has a pH from about 4.5 to about 8.0.

10. The composition of claim 9, where the compound is:

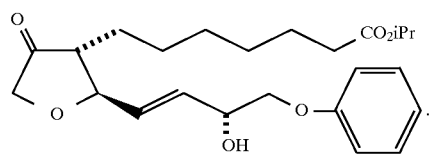

* * * * *